(12) United States Patent
Conklin et al.

(10) Patent No.: US 11,842,491 B2
(45) Date of Patent: Dec. 12, 2023

(54) NOVEL, QUANTITATIVE FRAMEWORK FOR THE DIAGNOSTIC, PROGNOSTIC, AND THERAPEUTIC EVALUATION OF SPINAL CORD DISEASES

(71) Applicant: Thomas Jefferson University, Philadelphia, PA (US)

(72) Inventors: Christopher J. Conklin, Philadelphia, PA (US); Feroze B. Mohamed, Philadelphia, PA (US); Devon M. Middleton, Philadelphia, PA (US); Mahdi Alizadeh, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 337 days.

(21) Appl. No.: 17/251,513

(22) PCT Filed: Jun. 14, 2019

(86) PCT No.: PCT/US2019/037196
§ 371 (c)(1),
(2) Date: Dec. 11, 2020

(87) PCT Pub. No.: WO2019/241637
PCT Pub. Date: Dec. 19, 2019

(65) Prior Publication Data
US 2021/0279877 A1   Sep. 9, 2021

Related U.S. Application Data

(60) Provisional application No. 62/685,137, filed on Jun. 14, 2018.

(51) Int. Cl.
G06K 9/00 (2022.01)
G06T 7/00 (2017.01)
(Continued)

(52) U.S. Cl.
CPC ............ *G06T 7/0014* (2013.01); *A61B 5/055* (2013.01); *A61B 5/4566* (2013.01);
(Continued)

(58) Field of Classification Search
CPC ........ A61B 2034/105; A61B 2034/101; A61B 5/4566; A61B 5/055; A61B 5/7267;
(Continued)

(56) References Cited

U.S. PATENT DOCUMENTS

2006/0229856 A1   10/2006   Burrus
2012/0280686 A1   11/2012   White
(Continued)

OTHER PUBLICATIONS

Alizadeh M, Conklin CJ, Middleton DM, Shah P, Saksena S, Krisa L, Finsterbusch J, Faro SH, Mulcahey MJ, Mohamed FB. Identification of ghost artifact using texture analysis in pediatric spinal cord diffusion tensor images. Magn Reson Imaging. Apr. 2018;47:7-15. doi: 10.1016/j.mri.2017.11.006. Epub Nov. 15, 2017. PMID: 29154897; PMCID: PMC5905435.
(Continued)

*Primary Examiner* — Atiba O Fitzpatrick
(74) *Attorney, Agent, or Firm* — Riverside Law LLP

(57) ABSTRACT

A method of generating a quantitative characterization of injury presence and status of spinal cord tissue using an adaptive CNN system for use in diagnostic assessment, surgical planning, and therapeutic strategy comprises preprocessing for artifact correction of diffusion based, spinal cord MRI data, training an adaptive CNN system with healthy and abnormal (injured/pathologic) spinal cord images obtained by imaging a population of healthy, typically developed spinal cord subjects and subjects with spinal cord injury, evaluating a novel, diffusion-based MRI image for injury biomarkers using the adaptive CNN system, generating a three-dimensional predictive axonal damage map for quantitative characterization and visualization of the (Continued)

novel, diffusion-based MRI image, and transmitting the sets of healthy and injured spinal cord images back to a central database for continued improvement of the adaptive CNN system training. A system for defining a predictive spinal axonal damage map is also described.

19 Claims, 4 Drawing Sheets

(51) Int. Cl.
*A61B 34/10* (2016.01)
*G06T 7/187* (2017.01)
*G06T 7/136* (2017.01)
*G06T 7/155* (2017.01)
*G16H 20/40* (2018.01)
*A61B 5/055* (2006.01)
*A61B 5/00* (2006.01)
*G06T 11/00* (2006.01)

(52) U.S. Cl.
CPC .......... *A61B 5/7214* (2013.01); *A61B 5/7267* (2013.01); *A61B 34/10* (2016.02); *G06T 7/136* (2017.01); *G06T 7/155* (2017.01); *G06T 7/187* (2017.01); *G06T 11/005* (2013.01); *G16H 20/40* (2018.01); *A61B 2034/105* (2016.02); *G06T 2207/10092* (2013.01); *G06T 2207/20081* (2013.01); *G06T 2207/20084* (2013.01); *G06T 2207/30012* (2013.01); *G06T 2211/424* (2013.01)

(58) Field of Classification Search
CPC ...... A61B 5/7264; G16H 50/30; G16H 50/20; G16H 15/00; G06T 17/00; G06T 17/005; G06T 17/05; G06T 17/10; G06T 17/20; G06T 17/205; G06T 17/30; G06T 2200/00; G06T 2200/04; G06T 2200/08; G06T 2200/24; G06T 2210/41; G06T 2207/30012; G06T 2207/10088; G06T 2207/10092; G06T 2207/20081; G06T 2207/20084; G16B 45/00; G06V 2201/033; G06V 10/70; G06V 10/82; G06V 10/774–7796; G01R 33/56341; G06K 9/6256; G06K 9/6257; G06K 9/6259; G06N 3/02–126; G06N 20/00–20; G06N 3/0464

See application file for complete search history.

(56) References Cited

U.S. PATENT DOCUMENTS

| | | | |
|---|---|---|---|
| 2015/0293200 A1* | 10/2015 | Kurpad | A61B 5/407 600/410 |
| 2017/0039708 A1 | 2/2017 | Henry | |
| 2017/0112575 A1* | 4/2017 | Li | A61B 34/10 |
| 2017/0273593 A1* | 9/2017 | Kiraly | A61B 5/7264 |
| 2018/0049665 A1* | 2/2018 | Jeong | A61B 5/055 |
| 2018/0256264 A1* | 9/2018 | McLachlin | A61B 5/0035 |
| 2019/0021677 A1* | 1/2019 | Grbic | G06T 7/11 |
| 2019/0328460 A1* | 10/2019 | Ronen | A61B 34/20 |
| 2019/0343418 A1* | 11/2019 | Kiraly | A61B 5/407 |
| 2020/0320786 A1* | 10/2020 | Kadoury | A61B 5/4566 |
| 2020/0405399 A1* | 12/2020 | Steinberg | G06N 20/00 |

OTHER PUBLICATIONS

Conklin, et al, Spatially selective 2D RF inner field of view (iFOV) diffusion kurtosis imaging (DKI) of the pediatric spinal cord. NeuroImage: Clinical. 2016, 7 pages.

International Search Report and Written Opinion issued in App. No. PCT/US2019/037196, dated Oct. 30, 2019, 10 pages.

Kamnitsas, et al., "Efficient multi-scale 3D CNN with fully connected CRF for accurate brain lesion segmentation," Medical Image Analysis,Oxford University Press, Oxofrd, GB, vol. 36, pp. 61-78.

Middleton, et al., An investigation of motion correction algorithms for pediatric spinal cord DTI in healthy subjects and patients with spinal cord injury. Magnetic Resonance Imaging, 2014, 7 pages.

Newcombe, et al., "Mapping Traumatic Axonal Injury Using Diffusion Tensor Imaging: Correlations with Functional Outcome," PLoS ONE, vol. 6, Nr: 5, pp. e19214.

* cited by examiner

NOVEL, QUANTITATIVE FRAMEWORK FOR THE DIAGNOSTIC, PROGNOSTIC, AND THERAPEUTIC EVALUATION OF SPINAL CORD DISEASES

CROSS-REFERENCE TO RELATED APPLICATIONS

This application is a U.S. national phase application filed under 35 U.S.C. § 371 claiming benefit to International Patent Application No. PCT/US2019/037196, filed Jun. 14, 2019, which is entitled to priority under 35 U.S.C. § 119(e) to U.S. Provisional Patent Application No. 62/685,137, filed Jun. 14, 2018, each of which applications is hereby incorporated herein by reference in its entirety.

STATEMENT REGARDING FEDERALLY SPONSORED RESEARCH OR DEVELOPMENT

This invention was made with government support under 5R01NS079635 awarded by the National Institutes of Health. The government has certain rights in the invention.

FIELD OF THE INVENTION

This application is generally related to methods for providing a quantitative assessment of the functional characteristics of the human spinal cord through generation of a predictive axonal damage map to identify different injury or diseased states along the entirety of the spinal cord.

BACKGROUND OF THE INVENTION

MRI imaging has provided a dramatic ability to visualize certain soft tissues in the body. After a traumatic or non-traumatic injury to the spinal cord, the affected individual will routinely undergo a series of evaluations to assess the condition, and possible damage to the spinal cord. To assess clinical status of motor and sensory functions, clinicians typically use the International Standards for Neurological Classification of Spinal Cord Injury (ISNCSCI). While some components, including of motor examination is completed through testing of key muscle functions, the sensory examination tests both light touch and sharp-dull discrimination on 28 different dermatomes on both sides of the body.

In general, the outcomes of the ISNCSCI exam are valid when looking at adult spinal cord injury cases. However there is substantial evidence that these examinations are not suitable for or applicable or accurate for pediatric populations.

Indeed, a major shortcoming of ISNCSI examinations is the absence of quantifiable data and is very subjective. However, there is variability between persons administering the examination, and quantifiable data can be obtained through magnetic resonance (MR) techniques, such as diffusion tensor imaging (DTI) and diffusion tensor tractography (DTT). These methods can be utilized to differentiate white matter and gray matter in the spinal cord. White matter structures consist of fibers/tracts that are ascending or descending and carry information to or from the brain to the rest of the body. Myelination ensures insulation of these tracts to restrict perpendicular flow. Accordingly, diffusion results in predominantly longitudinal flow. Gray matter, by contrast, is not characterized by organization with myelin and is therefore largely disordered, having highly isotropic diffusion patterns. In cases of injury or disease, anisotropic diffusion loss can be found resulting from axonal damage or pathologic degeneration of myelin.

As the performance of magnetic resonance imaging (MRI) improves, the number or DTI studies of the spinal cord has increased. However, these studies are often inconclusive. For example, a patient presents clear spinal cord damage, through their ISNCSI score or through motor function, yet the spinal cord damage is difficult to image or visualize to confirm the precise damage that causes the injury to the patient. Indeed, even where radiologists can identify an abnormality in an image, there is often still disagreement between clinical and MRI scores that leads to frustration and inconclusive results.

As described herein is a method as well as systems and platforms for generating clear, concise, and accurate quantifiable assessments for diffusion-based MRI scans of the spinal cord to aid in diagnosis and treatment of patients suffering from traumatic or non-traumatic spinal cord injuries.

SUMMARY OF THE INVENTION

The embodiments herein detail a method of evaluating a spinal cord injury through MRI, comprising generating a quantitative result of MRI scans. Through the generation of a set of quantitative, diffusion-based imaging biomarkers, a level by level (along the spinal cord) visualization of abnormal functional characteristics is created, which will allow for greater accuracy in clinical assessment and for qualitative or quantitative measures for quality control.

Ultimately, the methods are formulated via software systems running on a computer capable of accepting MRI images.

A preferred embodiment is directed towards a method of generating a quantitative characterization of injury presence and status of spinal cord tissue for use in diagnostic assessment, surgical planning, and therapeutic strategy comprising: Preprocessing scheme for artifact correction of diffusion based, spinal cord MRI data; Training an adaptive convolutional neural network (CNN) system with healthy and abnormal spinal cord images obtained by imaging a population of healthy, typically developed spinal cord subjects, and abnormal (injured/pathologic) spinal cords; Evaluating a novel, diffusion based MRI image for injury biomarkers using the adaptive CNN system; Generating a three-dimensional predictive axonal damage map for quantitative characterization and visualization of the novel, diffusion-based MRI image; and Transmitting the sets of healthy and injured spinal cord images back to a central database for continued improvement of the adaptive CNN system training.

In certain preferred embodiments, the predictive axonal damage map is utilized during performance of a surgical procedure.

A preferred embodiment is directed towards a method of generating a quantitative characterization of injury presence and status of spinal cord tissue using an adaptive CNN system for use in diagnostic assessment, surgical planning, and therapeutic strategy comprising: Preprocessing scheme for artifact correction of diffusion based, spinal cord MRI data; Training an adaptive CNN system with healthy and abnormal spinal cord images obtained by imaging a population of healthy, typically developed spinal cord subjects, and abnormal (injured/pathologic) spinal cords; Evaluating a novel, diffusion based MRI image for injury biomarkers using the adaptive CNN system; and generating a three-dimensional predictive axonal damage map for quantitative characterization and visualization of the novel, diffusion based MRI image.

In a preferred embodiment, a further step comprises transmitting the sets of healthy and injured spinal cord images back to a central database for continued improvement of the adaptive CNN system training.

In a preferred embodiment, the method further comprising: The capture and storage of diffusion sensitized MRI data, such data may include: Diffusion Tensor Imaging (DTI) data; Diffusion Kurtosis Imaging (DKI) data; Neurite Orientation Dispersion and Density Imaging (NODDI) data; and Other higher order diffusion sampling schema; wherein Artifact correction of the diffusion based MRI data which can but does not explicitly mandate the inclusion of noise reduction, eddy current correction, segmentation of the spinal cord, ghost artifact removal, coregistration and motion correction (realignment), and automated image quality control; Estimation and calculation of the diffusion tensor, kurtosis tensor, and multi-compartment models (e.g. NODDI) using an iteratively reweighted outlier rejection scheme; Texture analysis to extract relevant $1^{st}$ order, $2^{nd}$ order, higher order, as well as geometric image features for texture training of the adaptive CNN system; and Inclusion of healthy volunteer and injured spinal cord datasets, processed as detailed above, for continued diagnostic training of the adaptive CNN system.

In a preferred embodiment, the method further comprising: wherein the diffusion sensitized data (e.g. DTI, DKI, NODDI) is captured and stored.

In a preferred embodiment, the method further comprising wherein the pre-processing comprises a step of noise reduction based on a principal component analysis (PCA) method for signal decomposition and elimination of noise.

In a preferred embodiment, the method further comprising wherein the pre-processing comprises a step of eddy current correction based on estimation of the eddy current (EC) distortion field.

In a preferred embodiment, the method further comprising, wherein the pre-processing comprises a step of segmentation of the cord using histogram thresholding for tissue classification, morphological processing, and region growing techniques.

In a preferred embodiment, the method further comprising wherein the pre-processing comprises a step of ghost artifact removal based on texture analysis and automated classification using neuro-adaptive fuzzy logic.

In a preferred embodiment, the method further comprising wherein the pre-processing comprises a step of co-registration and realignment based on maximized mutual information and a variable degree of freedom transformation.

In a preferred embodiment, the method further comprising wherein the pre-processing module comprises an automated image quality control step based on local SNR characteristics, Euclidean metrics, and tissue contrast.

In a preferred embodiment, the method further comprising wherein the pre-processing module comprises a tensor estimation step unique to the sampling scheme used (e.g. DTI, DKI, NODDI).

In a preferred embodiment, the method further comprising wherein the pre-processing module comprise an outlier rejection step based on iteratively reweighting individual diffusion sensitized images based on residuals during the tensor estimation process.

In a preferred embodiment, the method further comprising wherein after completion of a pre-processing module, a pattern recognition module is employed.

In a preferred embodiment, the method further comprising wherein a pattern recognition module comprises histogram textures e.g. image intensity, variance, entropy, skewness, and kurtosis.

In a preferred embodiment, the method further comprising wherein a pattern recognition module comprises $2^{nd}$ order textures e.g. co-occurrence matrix contrast, homogeneity, correlation, and energy at 45° intervals.

In a preferred embodiment, the method further comprising wherein a pattern recognition module comprises higher order textures e.g. mean, variance, entropy, and energy of vertical, horizontal, and diagonal wavelet components.

In a preferred embodiment, the method further comprising wherein a pattern recognition module comprises geometric textures e.g. edge, corner, roundness, elasticity, and solidness.

In a preferred embodiment, the method further comprising wherein a pattern recognition module comprises histogram textures, $2^{nd}$ order textures, higher order textures, and geometric textures, and statistical testing of the same to determine feature relevance for the adaptive CNN system.

In a preferred embodiment, the method further comprising where training an adaptive CNN system using the captured and processed diffusion sensitized MR data (e.g. DTI, DKI, NODDI) and associated texture information for normal subjects and injured subjects.

In a preferred embodiment, the method further comprising wherein the trained adaptive CNN system classifies imaged tissue from patients as likely to be injured or not likely to be injured based on the aforementioned training using normative diffusion sensitized MR data.

In a preferred embodiment, the method further comprising any one of or a combination of the embodiments, which alone or in combination are utilized for capture of MRI data, post processing of said data, training of an adaptive CNN, and for generating a three-dimensional predictive axonal damage map.

In a preferred embodiment, the method further comprising generating a quantitative, three-dimensional predictive axonal damage map for the spinal cord; Wherein output from the trained, adaptive CNN will provide the quantitative information needed to characterize the presence, location, and extent of spinal cord injury on a per subject basis.

In a preferred embodiment, the method further comprising identifying injury to a spinal cord, wherein the predictive axonal damage map will be used by clinicians, surgeons, physical therapists, and PM&R physicians and therapists for reporting, surgical planning, and therapeutic strategy, for example: the map is used to precisely localize candidate sites for gene therapy with greater specificity than is possible through conventional MR imaging as well as the tracking of therapeutic outcomes by examining changes in microstructural diffusion properties over the course of treatment.

In a preferred embodiment, the method further comprising wherein the predictive axonal damage map is imported to a neuronavigational system, such as a Stryker or Medtronic system: Wherein the map is imported as a 3-D image to the neuronavigational system; and Wherein the map is overlaid onto conventional, structural MR imaging to provide the clinician with a real time view, location, and extent of tissue damage during surgical procedures.

In a preferred embodiment, the method further comprising wherein the diffusion sensitized image features (e.g. diffusion metrics, histogram, $1^{st}$, $2^{nd}$ and higher order texture values) are transmitted and stored on a centralized database for continued improvement of the adaptive CNN system training.

A preferred embodiment is directed towards a system for defining a predictive spinal axonal damage map comprising: a processor; a memory device comprising instructions, which when executed by the processor, cause the processor to: access a patient derived data comprising an MRI image; using the patient derived data as an input to an adaptive CNN system, the training of said adaptive CNN system using normative diffusion and texture values of said derived data to classify spinal cord images as healthy or abnormal; generating a three-dimensional predictive axonal damage map for quantitative characterization and visualization of the MRI image.

The system further comprising wherein said MRI image is preprocessed for artifact correction of diffusion based spinal cord MRI data.

The system further comprising wherein the patient derived data is of a healthy MRI image.

The system further comprising wherein the patient derived data is an MRI image of a damaged spinal cord.

The system further comprising: utilizing a preprocessing scheme for artifact correction of diffusion based, spinal cord MRI data; Training an adaptive CNN system with spinal cord images obtained by imaging a population of healthy, typically developed spinal cord subjects and abnormal (injured/pathologic) spinal cords; Evaluating a novel, diffusion based MRI image for injury biomarkers using the adaptive CNN system; Generating a three-dimensional predictive axonal damage map for quantitative characterization and visualization of the novel, diffusion based MRI image; and Transmitting the sets of healthy and injured spinal cord images back to a central database for continued improvement of the adaptive CNN system training.

In a further preferred embodiment, a system comprising: the capture and storage of diffusion sensitized MRI data, such data may include: Diffusion Tensor Imaging (DTI) data; Diffusion Kurtosis Imaging (DKI) data; Neurite Orientation Dispersion and Density Imaging (NODDI) data; Other higher order diffusion sampling schema; Artifact correction of the diffusion based MRI data which can but does not explicitly mandate the inclusion of noise reduction, eddy current correction, segmentation of the spinal cord, ghost removal, coregistration and motion correction (realignment), and automated image quality control; Estimation and calculation of the diffusion tensor, kurtosis tensor, and multi-compartment models (e.g. NODDI) using an iteratively reweighted outlier rejection scheme; Texture analysis to extract relevant $1^{st}$ order, $2^{nd}$ order, higher order, as well as geometric image features for texture training of the adaptive CNN system; and Inclusion of healthy volunteer and injured spinal cord datasets, processed as detailed above, for continued diagnostic training of the adaptive CNN system.

The system further comprising: wherein said training data set comprises a large cohort of MRI images of healthy spinal cords and abnormal (injured/pathologic) spinal cords.

The system further comprising, wherein the diffusion sensitized data (e.g. DTI, DKI, NODDI) is captured and stored.

The system further comprising wherein the pre-processing comprises a step of noise reduction based on a principal component analysis (PCA) method for signal decomposition and elimination of noise.

The system further comprising wherein the pre-processing comprises a step of eddy current correction based on estimation of the eddy current (EC) distortion field.

The system further comprising wherein the pre-processing comprises a step of segmentation of the cord using histogram thresholding for tissue classification, morphological processing, and region growing techniques.

The system further comprising wherein the pre-processing comprises a step of ghost artifact removal based on texture analysis and automated classification using neuro-adaptive fuzzy logic.

The system further comprising wherein the pre-processing comprises a step of co-registration and realignment based on maximized mutual information and a variable degree of freedom transformation.

The system further comprising wherein the pre-processing module comprises an automated image quality control step based on local SNR characteristics, Euclidean metrics, and tissue contrast.

The system further comprising wherein the pre-processing module comprises a tensor estimation step unique to the sampling scheme used (e.g. DTI, DKI, NODDI).

The system further comprising wherein the pre-processing module comprise an outlier rejection step based on iteratively reweighting individual diffusion sensitized images based on residuals during the tensor estimation process.

The system further comprising wherein after completion of a pre-processing module, a pattern recognition module is employed.

The system further comprising wherein a pattern recognition module comprises histogram textures e.g. image intensity, variance, entropy, skewness, and kurtosis.

The system further comprising wherein a pattern recognition module comprises $2^{nd}$ order textures e.g. co-occurrence matrix contrast, homogeneity, correlation, and energy at 45° intervals.

The system further comprising, wherein a pattern recognition module comprises higher order textures e.g. mean, variance, entropy, and energy of vertical, horizontal, and diagonal wavelet components.

The system further comprising, wherein a pattern recognition module comprises geometric textures e.g. edge, corner, roundness, elasticity, and solidness.

The system further comprising, wherein a pattern recognition module comprises histogram textures, $2^{nd}$ order textures, higher order textures, and geometric textures, and statistical testing of the same to determine feature relevance for the adaptive CNN system, where training an adaptive CNN system using the captured and processed diffusion sensitized MR data (e.g. DTI, DKI, NODDI) and associate texture information for normal subjects and subjects with spinal cord injury.

The system further comprising, wherein the trained adaptive CNN system classifies imaged tissue from patients as likely to be injured or not likely to be injured based on the aforementioned training using normative diffusion sensitized MR data.

The system further comprising generating a quantitative, three-dimensional predictive axonal damage map for the spinal cord; wherein output from the trained, adaptive CNN system will provide the quantitative information needed to characterize the presence, location, and extent of spinal cord injury on a per subject basis;

The system further comprising identifying injury to a spinal cord, wherein the predictive axonal damage map will be used by clinicians, surgeons, physical therapists, PM&R staff for reporting, surgical planning, and therapeutic strategy, for example: the map is used to precisely localize candidate sites for gene therapy with greater specificity than is possible through conventional MR imaging as well as the tracking of therapeutic outcomes by examining changes in microstructural diffusion properties over the course of treatment.

The system further comprising wherein the predictive axonal damage map is imported to a neuronavigational system, such as a Stryker or Medtronic system: wherein the map is imported as a 3-D image to the neuronavigational system; and wherein the map is overlaid onto conventional, structural MR imaging to provide the clinician with a real time view, location, and extent of tissue damage during surgical procedures.

The system further comprising wherein the diffusion sensitized image features (e.g. diffusion metrics, histogram, $1^{st}$, $2^{nd}$, and higher order texture values) are transmitted and stored on a centralized database for continued improvement of the adaptive CNN system training.

A method of diagnosing a patient exhibiting spinal cord damage comprising: use of the method of any one of the above embodiments to generate a predictive axonal damage map, wherein said predictive axonal damage map is imported into a neuronavigational system for performing a surgical procedure.

The above embodiments are advantageously used along or in combination with one or more of the embodiments to generate a new and useful method and system for capturing images of normal and injured spinal cords, said images captured as MRI images and said images are processed via the methods described above; said processed MRI images form the basis for a training dataset to define parameters for a healthy and injured spinal cord. Said parameters then define the adaptive CNN system, and wherein a novel, clinical MRI image can be evaluated by said adaptive CNN system to determine presence and location of cord injury.

DETAILED DESCRIPTION OF THE EMBODIMENTS

Figure 1:
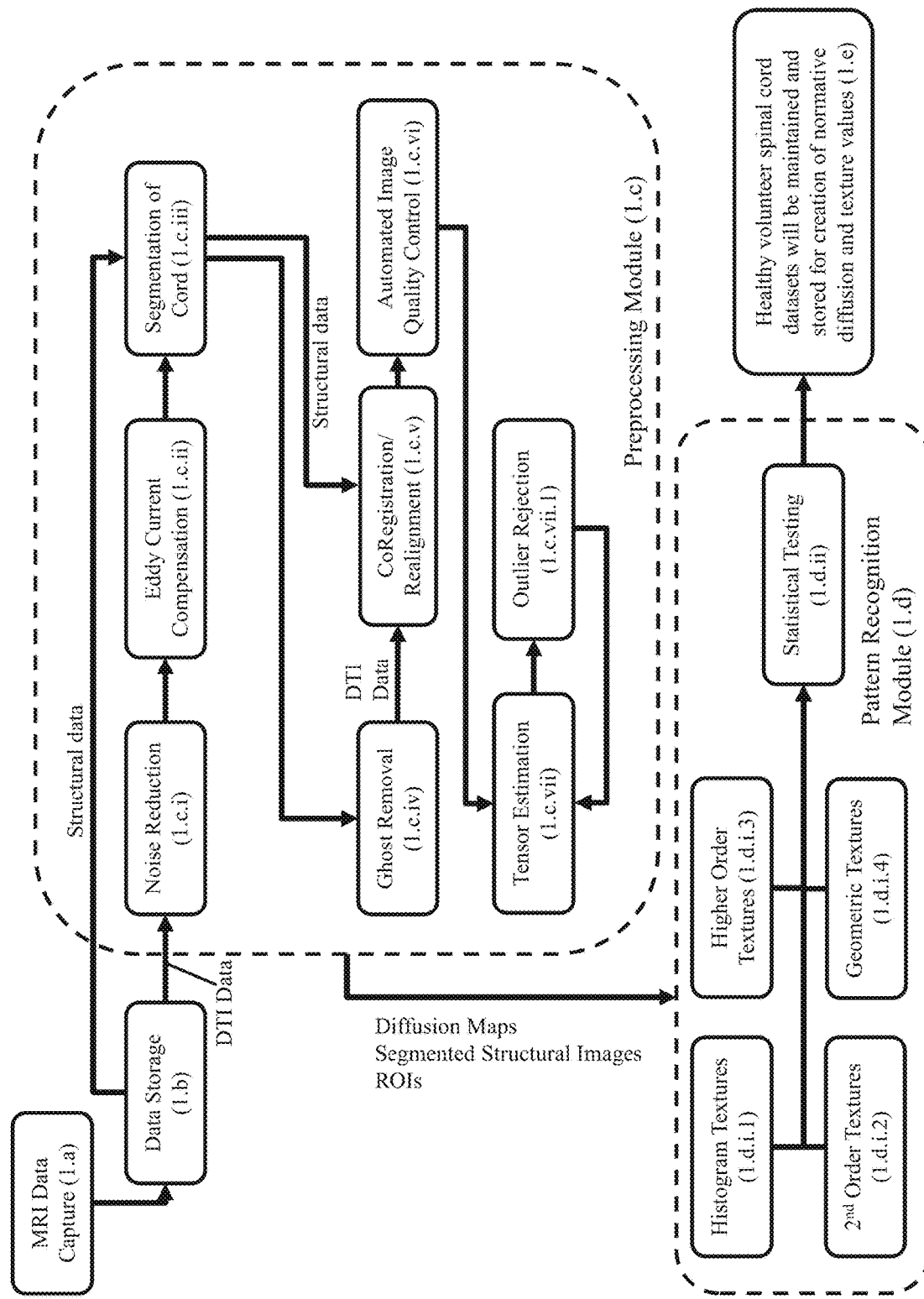
FIG. 1 depicts a flowchart depicting the processing of diffusion sensitized MR data for storage in a centralized database for use in determination of functionally normal/abnormal spinal cord via training of an adaptive CNN system.

It is to be understood that the figures and descriptions of the present invention have been simplified to illustrate elements that are relevant for a clear understanding of the present invention, while eliminating, for the purpose of clarity, many other elements found in related systems and methods. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C #, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

MRI imaging has led to dramatic increases in visualization capabilities for soft tissues. However, with the advances, there remains a high level of uncertainty because imaging software becomes abstract, in the sense that there is not always a binary answer regarding damaged tissue and whether such damage is attributable to a particular ailment suffered by a patient.

However, continued advances in MRI devices provide for sufficiently clear images that we can utilize deep learning (i.e. adaptive CNN system), as well as various image pre and post processing procedures to generate better data, clearer data, and data that can be quantified, mapped, and ultimately utilized to detect spinal cord injury, determine the extent of said injury, and for planning procedures regarding surgical or other treatments to the tissue site.

Herein, we describe methods and systems that utilize machine learning to better identify damage to spinal tissues. Preferably, the method comprises one or more of the modules described herein, provided alone or together in combination. When used together, the entire method utilizes a data set of healthy and abnormal spinal tissue to generate a data learning set for adaptive CNN (AI learning). From there, the methods comprise utilizing said data learning set on new data or images and finally the new data or images are analyzed by the adaptive CNN system trained by the aforementioned learning set to generate a quantitative, three-dimensional predictive axonal damage map. In preferred embodiments, the three-dimensional predictive axonal damage map can be utilized to perform surgical procedures, treat the patient with therapeutics, or applying or performing other procedures to improve or impact the spinal cord.

In further embodiments, certain methods and steps can be utilized together to generate a centralized database for use in determination of functionally normal or abnormal spinal cords via an adaptive CNN system. In particular, we can utilize the power of numbers to aggregate healthy and injured/pathologic spinal cord images from FIG. 1 and generate a set of data that is maintained and stored for creating of normative diffusion and texture values within a spinal cord. Such steps include the following as detailed in FIG. 1.

A first step MRI data capture (1.a) comprises wherein data captured using a Magnetic Resonance Imaging (MRI) device with diffusion sensitized acquisition schemes with sufficient shell definition at given accurate angular resolutions for optimal diffusion profile sampling will be used. High resolution anatomical imaging will also be performed along the spinal cord for vertebral level identification, segmentation, and coregistration purposes.

After the MRI data is captured, step 1.b in FIG. 1 confirms that Data will be pushed to either a local hard drive or server for storage prior to analysis.

After pushing the data to either a local hard drive or a server for storage, step 1.c comprises raw diffusion-based and structural MRI DICOM data will be pulled from the server or local hard drive and input to the preprocessing module. This preprocessing module comprises seven substeps and ends with an eighth step informing the seventh step via iterative outlier rejection.

Accordingly, in step 1.c.i, the raw diffusion dataset will first undergo noise reduction for high frequency signal component removal using Principal Component Analysis (PCA). Raw diffusion data has inherently low SNR as it is a signal attenuation measurement that is highly susceptible to noise (thermal, Rician) due to the fast echo planar imaging (EPI) acquisition schemes. PCA works by decomposing the diffusion MR signal into local principle components, down-weighting/eliminating unwanted components, and then reconstructing the signal. This has improved the signal quality to help ensure the most accurate calculated diffusion metrics.

After confirmation of the noise reduction steps, step 1.c.ii next performs eddy current (EC) correction. Gaussian processes are used to predict an eddy current free image based on calculated EC fields and then compared to the actual data. This is an iterative process that continues to refine the field estimates until predicted vs actual error is minimized. Eddy currents are prevalent in MR imaging due to the constant, oscillatory nature of the magnetic fields used for excitation and spatial encoding. They manifest in images as distortion that can warp or stretch the images along the phase encode direction.

After the iterative process refines the field estimates to minimize error, step 1.c.iii confirms that the structural MR data is fed to the segmentation block where the entirety of the spinal cord is defined, masked, and saved. This will be performed using histogram-based tissue classification and morphological processing techniques. Segmentation is important as it will enable more accurate realignment and thereby facilitate a more appropriate tensor fit.

After segmentation provides a more accurate realignment and facilitates a more appropriate tensor fit, step 1.c.iv details the ghost artifact removal technique. Ghost artifact removal is another critical preprocessing step that will remove some effects from pulsatile motion, which is prevalent in the spinal cord, and potential echo misalignment associated with EPI sequences. Spatial smoothing is performed using a median filter of appropriate window size and then the image is compressed to 8-bits to reduce sensitivity to noise bias. Morphological processing is applied to create and label a binary image. This image will be overlaid on the initial image to mask out both the real and ghost cord. Histogram-based and gray level co-occurrence texture measures will extract relevant information from both cords to remove the ghost artifact. This is achieved using a neuroadaptive fuzzy logic system.

After ghost removal and spatial smoothing of the image, step 1.c.v details the coregistration and motion correction of all resultant image volumes using mutual information-based methods and variable degrees of freedom based on diffusion data.

Registration/realignment is a critical step in ensuring that proper voxel to voxel correspondence is achieved for each directional image to provide the most accurate tensor fit.

Segmented structural images will be used to align the structural and functional images as well.

After segmented structural images are utilized to align the structural and functional images, step 1.c.vi utilizes an automated quality control check will be performed for rejection of low signal/attenuated slices or artifactually contaminated slices through subject specific, adaptive threshold definition. This will further enhance the accuracy of the tensor fit.

Finally, step 1.c.vii outlines that the tensor estimation is the step that characterizes and quantifies the diffusion information contained within the acquired, and now preprocessed dataset. DTI analysis is the simplest as the model assumes an ideal Gaussian water distribution and each voxel is considered a single compartment. Kurtosis analysis (DKI) is a refinement in that while it also assumes a single compartment, the underlying displacement distribution is measured in terms of its non-gaussianity. Neurite Orientation Dispersion and Density Imaging (NODDI) is the most sophisticated estimation scheme that is a three-compartment model broken up into CSF, white matter, and gray matter. This more rigorous model enables the quantification of neurite orientation and neurite density within a given voxel. The combination of these analyses forms a multispectral dataset that will serve as the input to the AI module for functional spinal cord characterization.

In certain applications, Outlier rejection is an iterative weighting approach that seeks to remove datapoints/voxels that will skew results. It is an additional correction scheme embedded in the tensor estimation algorithm to provide another layer of accuracy. The preprocessing module comprising the above steps can be used as a single step, including each of the elements to provide the most complete preprocessing of the MRI data. However, each of the individual steps can also be used in combination with 1, 2, 3, 4, 5, 6, 7, or all 8 steps, including any combination of each of the components 1-8.

After the preprocessing module is completed, the pattern recognition module is utilized to generate structural data. In Step 1.d, the Quantitative maps generated by the preprocessing module will be then feed into the Pattern Recognition (Texture) Module.

To meet the limitations of the pattern recognition module (1.d), four steps are necessary. Step 1.d.i. confirms that diffusion based quantitative maps, segmented structural images, and defined Regions of Interest (ROI) will be fed into four different texture blocks for image feature extraction. These features will facilitate a more comprehensive characterization of the diffusion and structural data.

These diffusion-based maps are generated via four additional steps:

Step 1.d.i.1: The histogram-based block will investigate the distribution of numerical values of interest, which may include the mean, standard deviation, kurtosis, etc. of the pixel/signal values contained within the ROI.

Step 1.d.i.2: The $2^{nd}$ order texture block will use a predefined window to calculate quantifiable image characteristics using a gray level co-occurrence matrix (GLCM) ranging from 0-135 degrees. These characteristics include homogeneity, correlation, and energy, as examples.

Step 1.d.i.3: The higher order texture block will look at diagonal, horizontal, and vertical wavelet decompositions of the image defined by the ROI. Values such as mean and energy, to name a few, will be determined for each wavelet component.

Finally, step 1.d.i.4: Geometric feature extraction such as edge and corner definition will also be done to collect further information. As with the preprocessing module above, each of the four steps can be used singly, or in combination with 1, 2, 3, or all 4 of the steps.

After the steps of the diffusion based quantitative maps, statistical testing is performed, according to step 1.d.ii: Statistical testing will be performed on each of the extracted features calculated from the four texture blocks. Feature vectors will be fed to the statistical module to evaluate their significance. A predefined statistical threshold will be used to select only the features of most importance.

Then, as defined in step 1.e, calculated healthy volunteer spinal cord datasets will be maintained and stored on a centralized server for creation of normative values. These normative metrics will serve as the level by level baseline values for determination of abnormality of an injured cord. Accordingly, the system described herein and the appropriate steps in the method generate a data set of a single MRI scan. When used with a library of healthy and injured MRI scans, we can collate the data and create a data set for training of an adaptive CNN. Indeed, these datapoints become the basis for the data set and serve as a normative value, and the standard deviations within this data set provide a range of "normal" and "abnormal" tissue for comparison and training of an adaptive CNN.

Ultimately, once the normative spinal cord levels have been determined, they will serve as an input to the adaptive CNN module and continually updated as more normal and abnormal spinal cord data is acquired or shared. These normative values will provide the AI system with the requisite, healthy and abnormal image feature ranges for comparison against a subject/patient with suspected spinal cord injury/pathology. For example, in a case where a subject/patient presents with clinical deficiencies yet no imaging evidence, this subject/patient's data will follow the aforementioned methodology to generate a vector set of imaging features. Once these features are passed to the AI system, they will be classified based on comparison to features from normal and abnormal spinal cords used in training of the system.

When a comparison is made, the system utilizes the known data set of normal and abnormal MRI scans and can then classify a new MRI scan, regardless of whether it is damaged or healthy. If the system determines that the current subject/patient's spinal cord is abnormal relative to what has been classified as normal or abnormal it will effective tag the locations where an abnormality exists.

Accordingly, the data generated through collection of MRI scans from healthy and injured/pathologic patients, as detailed in FIG. 1 is imported for use in generation of an adaptive CNN system for comparing the classified scans to an unknown MRI image. Thus, in further embodiment a method comprises, quantification of diffusion sensitized images of MRI data for diagnostic assessment via an adaptive CNN system. This embodiment is detailed in FIG. 2. Most preferentially, the methods of FIG. 1 can be utilized with additional steps and components as described herein.

A first step MRI data capture (2.a) comprises wherein data captured using a Magnetic Resonance Imaging (MRI) device with diffusion sensitized acquisition schemes with sufficient shell definition at given accurate angular resolutions for optimal diffusion profile sampling will be used. High resolution anatomical imaging will also be performed along the spinal cord for vertebral level identification, segmentation, and coregistration purposes.

After the MRI data is captured, step 2.b in FIG. 1 confirms that Data will be pushed to either a local hard drive or server for storage prior to analysis.

After pushing the data to either a local hard drive or a server for storage, step 2.c comprises raw diffusion-based and structural MRI DICOM data will be pulled from the server or local hard drive and input to the preprocessing module. This preprocessing module comprises seven sub steps and ends with an eighth step outlining certain rejections.

Accordingly, in step 2.c.i, the raw diffusion dataset will first undergo noise reduction for high frequency signal component removal using Principal Component Analysis (PCA). Raw diffusion data has inherently low SNR as it is a signal attenuation measurement that is highly susceptible to noise (thermal, Rician) due to the fast echo planar imaging (EPI) acquisition schemes. PCA works by decomposing the diffusion MR signal into local principle components, down-weighting/eliminating unwanted components, and then reconstructing the signal. This has improved the signal quality to help ensure the most accurate calculated diffusion metrics.

After confirmation of the noise reduction steps, step 1.c.ii next performs eddy current (EC) correction. Gaussian processes are used to predict an eddy current free image based on calculated EC fields and then compared to the actual data. This is an iterative process that continues to refine the field estimates until predicted vs actual error is minimized. Eddy currents are prevalent in MR imaging due to the constant, oscillatory nature of the magnetic fields used for excitation and spatial encoding. They manifest in images as distortion that can warp or stretch the images along the phase encode direction.

After the iterative process refines the field estimates to minimize error, step 2.c.iii confirms that the structural MR data is fed to the segmentation block where the entirety of the spinal cord is defined, masked, and saved. This will be performed using histogram-based tissue classification and morphological processing techniques. Segmentation is important as it will enable more accurate realignment and thereby facilitate a more appropriate tensor fit.

After segmentation provides a more accurate realignment and facilitates a more appropriate tensor fit, step 2.c.iv details the ghost removal technique. Ghost removal is another critical preprocessing step that will remove some effects from pulsatile motion, which is prevalent in the spinal cord, and potential echo misalignment associated with EPI sequences. Spatial smoothing is performed using a median filter of appropriate window size and then the image is compressed to 8-bits to reduce sensitivity to noise bias. Morphological processing is applied to create and label a binary image. This image will be overlaid on the initial image to mask out both the real and ghost cord. Histogram-based and gray level co-occurrence texture measures will extract relevant information from both cords to remove the ghost artifact. This is achieved using a neuro-adaptive fuzzy logic system.

After ghost removal and spatial smoothing of the image, step 2.c.v details that the coregistration and motion correction of all resultant image volumes using mutual information-based methods and variable degrees of freedom based on diffusion data. Registration/realignment is a critical step in ensuring that proper voxel to voxel correspondence is achieved for each directional image to provide the most accurate tensor fit. Segmented structural images will be used to align the structural and functional images as well.

After segmented structural images are utilized to align the structural and functional images, step 2.c.vi utilizes an automated quality control check will be performed for rejection of low signal/attenuated slices or artifactually contaminated slices through subject specific, adaptive threshold definition. This will further enhance the accuracy of the tensor fit.

Finally, after the tensor fit is complete, step 1.c.vii outlines that the tensor estimation is the step that characterizes and quantifies the diffusion information contained within the acquired, and now preprocessed dataset. DTI analysis is the simplest as the model assumes an ideal Gaussian water distribution and each voxel is considered a single compartment. Kurtosis analysis is a refinement in that while it also assumes a single compartment, the underlying displacement distribution is measured in terms of its non-gaussianity. Neurite Orientation Dispersion and Density Imaging (NODDI) is the most sophisticated estimation scheme that is a three-compartment model broken up into CSF, white matter, and gray matter. This more rigorous model enables the quantification of neurite orientation and neurite density within a given voxel. The combination of these analyses forms a multispectral dataset that will serve as the input to the AI module for functional spinal cord characterization.

In certain applications, Outlier rejection is an iterative weighting approach that seeks to remove datapoints/voxels that will skew results. It is an additional correction scheme embedded in the tensor estimation algorithm to provide another layer of accuracy.

After the preprocessing module is completed, the pattern recognition module is utilized to generate structural data. In Step 2.d, the Quantitative maps generated by the preprocessing module will be then fed into the Pattern Recognition (Texture) Module.

To meet the limitations of the pattern recognition module (2.d), four steps are necessary. Step 2.d.i. confirms that diffusion based quantitative maps, segmented structural images, and defined Regions of Interest (ROI) will be fed into four different texture blocks for image feature extraction. These features will facilitate a more comprehensive characterization of the diffusion and structural data.

These diffusion-based maps are generated via four additional steps:

Step 2.d.i.1: The histogram-based block will investigate the distribution of numerical values of interest, which may include the mean, standard deviation, kurtosis, etc. of the pixel/signal values contained within the ROI.

Step 2.d.i.2: The $2^{nd}$ order texture block will use a predefined window to calculate quantifiable image characteristics using a gray level co-occurrence matrix (GLCM) ranging from 0-135 degrees. These characteristics include homogeneity, correlation, and energy, as examples.

Step 2.d.i.3: The higher order texture block will look at diagonal, horizontal, and vertical wavelet decompositions of the image defined by the ROI. Values such as mean and energy, to name a few, will be determined for each wavelet component.

Finally, step 2.d.i.4: Geometric feature extraction such as edge and corner definition will also be done to collect further information.

After the steps of the diffusion based quantitative maps, statistical testing is performed, according to step 2.d.ii: Statistical testing will be performed on each of the extracted features calculated from the four texture blocks. Feature vectors will be fed to the statistical module to evaluate their significance. A predefined statistical threshold will be used to select only the features of most importance.

Ultimately, a vector set of statistically significant image features will be determined from the quantified, functional (diffusion sensitized) maps as well as the structural images to serve as input to the adaptive CNN system. Therefore, step 2.e confirms that statistically significant features from the Texture Module will be fed to the adaptive CNN system to make a determination as to whether the analyzed dataset meets the criteria for a functionally abnormal spinal cord.

The adaptive CNN module classifies input data from diffusion sensitized MR images as injured or non-injured. A training set of diffusion metrics and texture information derived from normative diffusion sensitized MR data collected from healthy and abnormal (injured/pathologic) spinal cords is initially provided to the adaptive CNN system. After training, the adaptive CNN system classifies tissues as injured or non-injured based on deviations of local diffusion metrics and image texture features to normative values established by the training set.

The output of the adaptive CNN module will provide a decision, within certain confidence limits as well as within appropriate specificity and sensitivity constraints, as to whether a functional, or physiological, abnormality exists for each level of the subject's spinal cord relative to classified, normative and abnormal values. This information would prove extraordinarily valuable to radiologists, surgeons, physical therapists, and PM&R doctors and researchers localize injury site non-invasively, quantifiably, and more reliably than current clinical standards when conventional imaging does not qualitatively suggest an abnormality. For example, for an individual subject/patient that presents with motor and/or sensory incomplete injury, as determined by an ISNCSI exam, yet shows no visible injury on conventional, clinical imaging, this system would provide quantifiable evidence to show location, extent, and severity of the injury. This would greatly facilitate more effective treatment plans as well as allow placement of stem cell delivery vectors (e.g. viral) to a precise area of the cord to stimulate regrowth of damaged white matter tracts. In more severe cases, it would also allow for three-dimensional visualization and subsequent translation to a surgical environment as outlined below.

Accordingly, in a preferred embodiment, we capture healthy and abnormal MRI data and generate confidence limits, within the appropriate specificity and sensitivity constrains. By capturing such data, we can generate a high level of confidence for comparison to a novel MRI image, and determine from the novel MRI image the status of localized injury, if any. This novel image can be added to the training dataset for further development and training of the adaptive CNN after classification.

Figure 2:
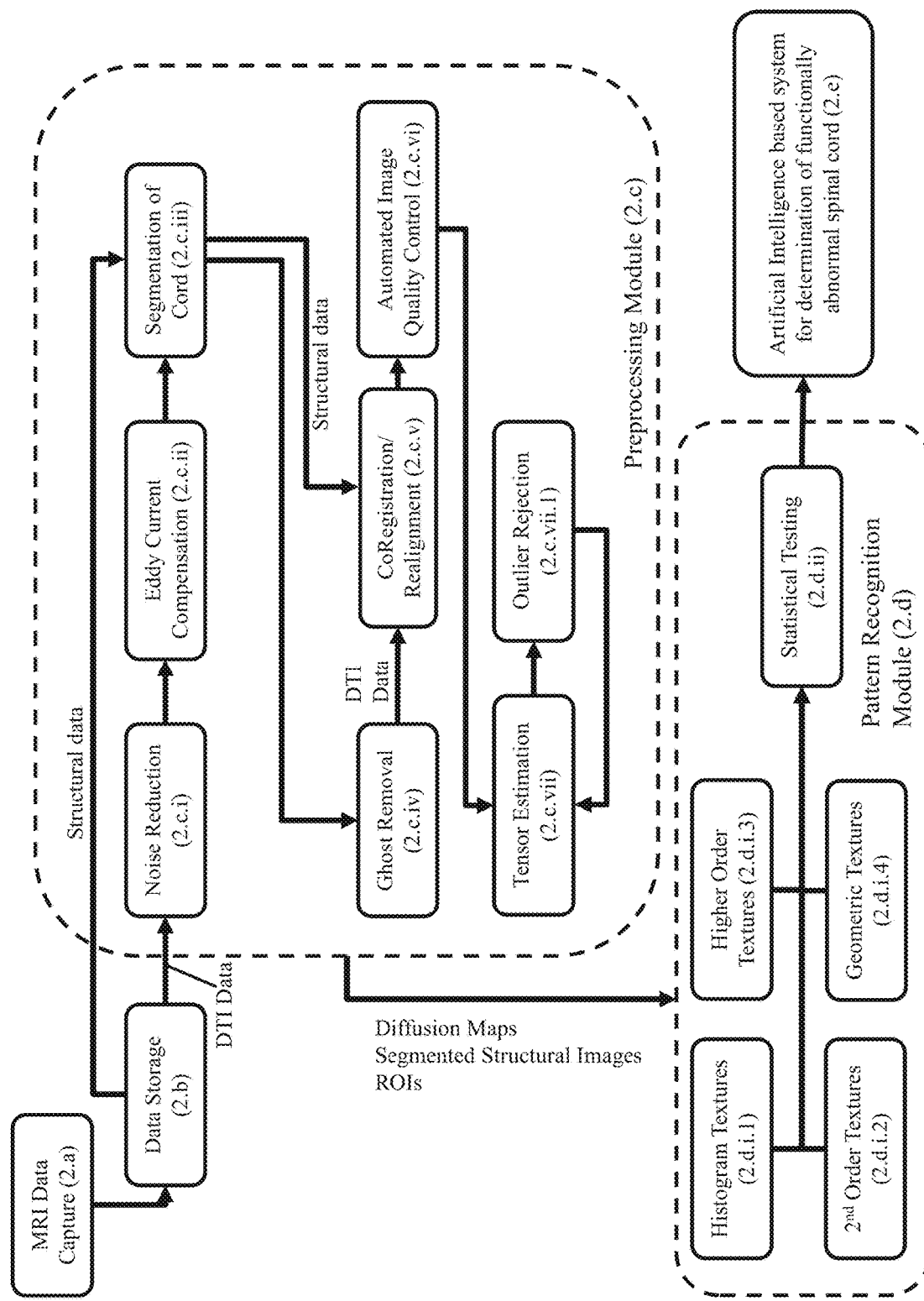
FIG. 2 depicts a flowchart for a method of using an adaptive CNN system for quantitative diffusion sensitized image analysis and classification of non-injured/injured spinal cord tissue.

Once the above steps are performed, as detailed in FIGS. 1 and 2, a complete set of data from healthy and abnormal spinal cords provides for a valuable comparison tool when a damaged spinal cord MRI is presented. Indeed, one of the largest concerns with MRI data is that a patient presents with clinical motor and/or sensory deficits indicative of spinal cord injury, but conventional clinical MRI data may not clearly show damage, or there is inconsistency of opinion of the location of damage. The methods and systems herein seek to eliminate this issue and to provide for a quantifiable set of parameters to visualize, map, and otherwise define damage to a spinal cord.

Importantly, the set of healthy and abnormal spinal cord data is provided into an adaptive CNN system to generate a trained machine to be able to compare a new MRI image to the trained machine. Because we have captured a data set of healthy and abnormal spinal cord images, the machine can be trained to classify spinal cord images as healthy or abnormal. Once a new image is provided, the machine is capable of generating a quantified response of the new MRI image and determine the risk of damage to the spinal cord in said MRI image.

Figure 3:
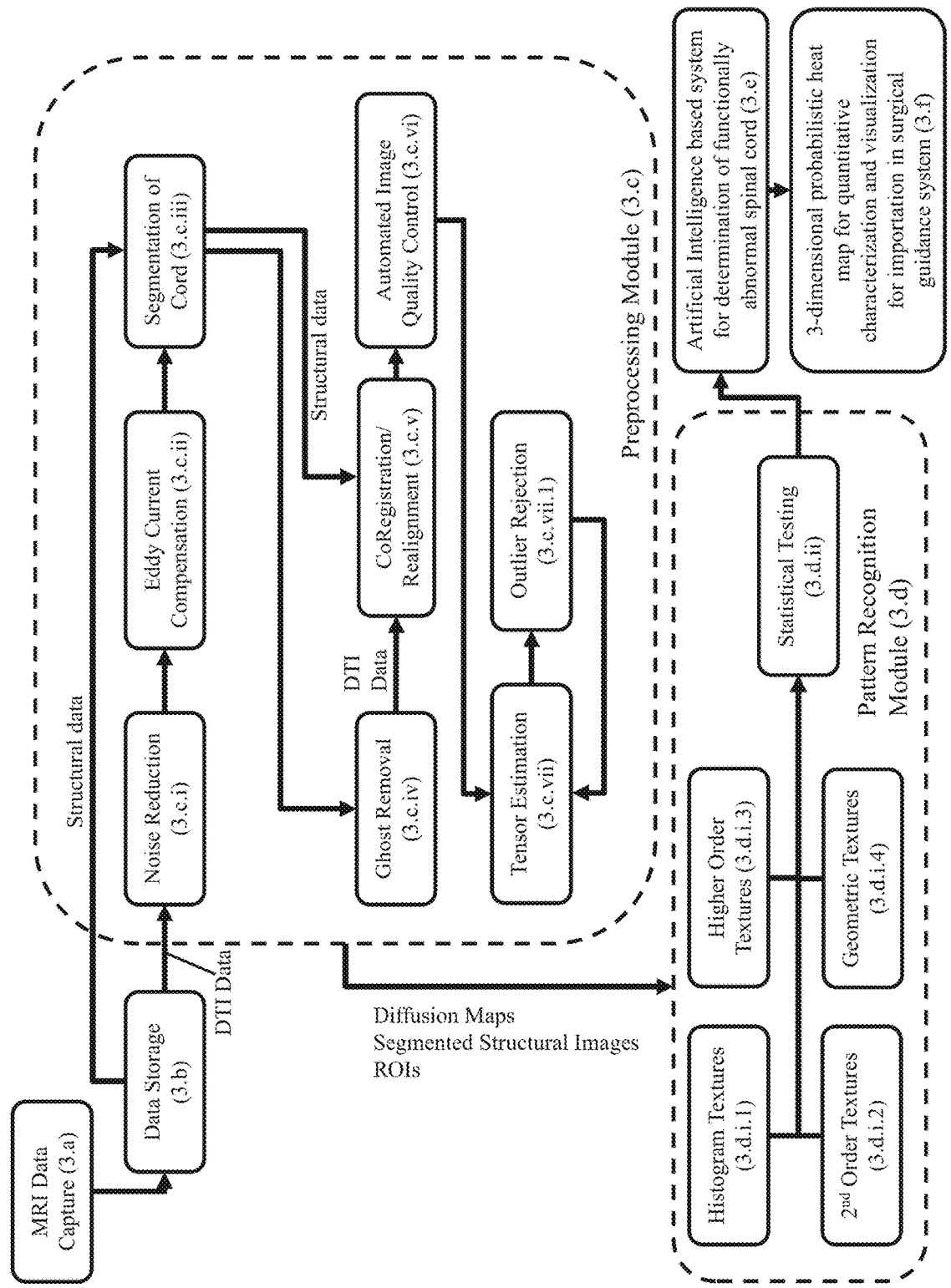
FIG. 3 depicts a flowchart depicting importing of predictive axonal damage maps into a neuronavigational system for enhancement of surgical planning and processes.

Accordingly, FIG. 3 details the ability to generate and import a predictive axonal damage map into a neuronavigational system for enhancement of surgical planning and process.

Figure 4:
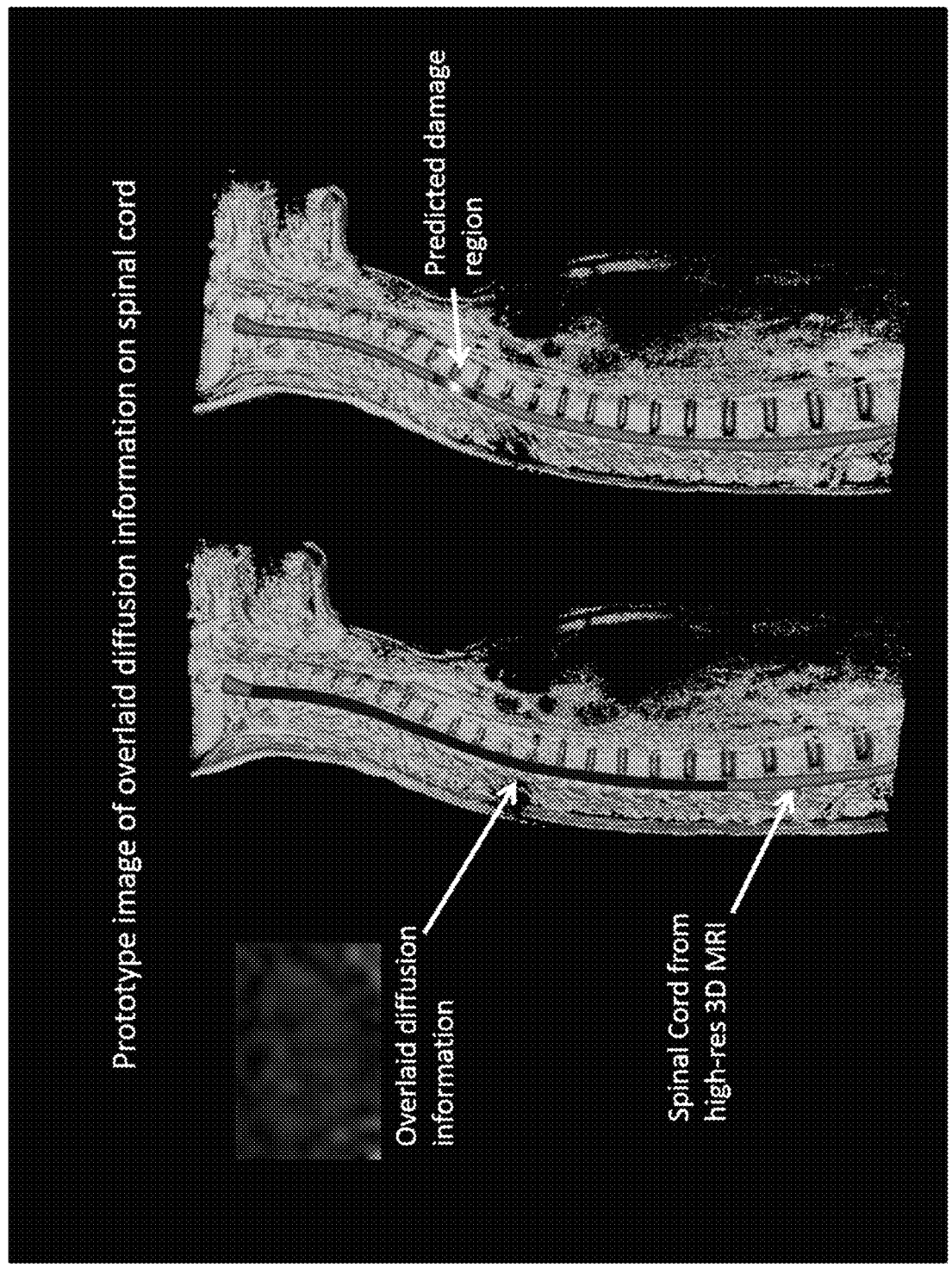
FIG. 4 depicts a prototype image of overlaid diffusion information on a 3-D spinal cord image captured using conventional MR and an overlaid predictive damage map.

FIG. 4 shows an example prototype image of the overlaid diffusion information and predictive damage map on a 3D representation of the spinal cord from conventional MR imaging. This method relies on the above described modules to create a healthy and abnormal training data set and then classify a new MRI image. The formation of a training dataset, therefore, serves as a foundational bedrock of the machine learning tool and the inclusion of the creation of normative spinal cord level ranges and the subsequent determination of injury location are necessary for the generation of the predictive axonal damage map. The predictive axonal damage map is a three-dimensional, subject-specific reconstruction of the spinal cord with overlaid, functional injury markers. This three-dimensional overlay allows the surgeon to determine the best possible route for entering the body based on where the injury is located. Thus, by generating a predictive map of injury, access can be determined and entry points can be evaluated for safety and efficacy with precision.

The image could also be linked to a neuronavigational system that would track and rotate based on the surgeon's maneuvers. Such neuronavigational systems are known in the art by such manufacturers as Stryker® and Medtronic®. The system can import the generated map which can be utilized for performing medical procedures. Accordingly, in a preferred embodiment, a system comprises a device having a visual display and said visual display is connected to a surgical tool. Said surgical tool is paired to the system allowing the rotation and movement along the path of an image displayed on said display, a current position of the surgical can be displayed with orientation to the surgeon. Visual orientation of the device can be applied by any number of camera tracking applications, or other positional tracking that can orient precise locations along the position of the spinal column, and a gyroscope, included within the surgical tool can orient the up or down, left or right aspects of the device.

Such an apparatus would greatly aid in providing the surgeon with a functional look of where the injury site(s) are relative to their position within the spinal cord. Not only does it give the surgeon a road map for choosing the best possible route for entry and for access to damaged tissue, but also gives them real-time positioning information as to where they are operating in comparison to the injury sites to allow for not only more accurate placement of hardware, stem cell vectors, and other surgical treatments, but also reduce the amount of time required to complete the procedure.

In importing spinal cord predictive axonal damage maps, as defined by FIG. 3, the method must first follow a standard set of protocols:

A first step MRI data capture (3.a) comprises wherein data captured using a Magnetic Resonance Imaging (MRI) device with diffusion sensitized acquisition schemes with sufficient shell definition at given accurate angular resolutions for optimal diffusion profile sampling will be used. High resolution anatomical imaging will also be performed along the spinal cord for vertebral level identification, segmentation, and coregistration purposes.

After the MRI data is captured, step 3.b in FIG. 1 confirms that Data will be pushed to either a local hard drive or server for storage prior to analysis.

After pushing the data to either a local hard drive or a server for storage, step 3.c comprises raw diffusion-based and structural MRI DICOM data will be pulled from the server or local hard drive and input to the preprocessing module. This preprocessing module comprises seven substeps and ends with an eighth step outlining certain rejections.

Accordingly, in step 3.c.i, the raw diffusion dataset will first undergo noise reduction for high frequency signal component removal using Principal Component Analysis (PCA). Raw diffusion data has inherently low SNR as it is a signal attenuation measurement that is highly susceptible to noise (thermal, Rician) due to the fast echo planar imaging (EPI) acquisition schemes. PCA works by decomposing the diffusion MR signal into local principle components, down-weighting/eliminating unwanted components, and then reconstructing the signal. This has improved the signal quality to help ensure the most accurate calculated diffusion metrics.

After confirmation of the noise reduction steps, step 1.c.ii next performs eddy current (EC) correction. Gaussian processes are used to predict an eddy current free image based on calculated EC fields and then compared to the actual data. This is an iterative process that continues to refine the field estimates until predicted vs actual error is minimized. Eddy currents are prevalent in MR imaging due to the constant, oscillatory nature of the magnetic fields used for excitation and spatial encoding. They manifest in images as distortion that can warp or stretch the images along the phase encode direction.

After the iterative process refines the field estimates to minimize error, step 3.c.iii confirms that the structural MR data is fed to the segmentation block where the entirety of the spinal cord is defined, masked, and saved. This will be performed using histogram-based tissue classification and morphological processing techniques. Segmentation is important as it will enable more accurate realignment and thereby facilitate a more appropriate tensor fit.

After segmentation provides a more accurate realignment and facilitates a more appropriate tensor fit, step 3.c.iv details the ghost removal technique. Ghost artifact removal is another critical preprocessing step that will remove some effects from pulsatile motion, which is prevalent in the spinal cord, and potential echo misalignment associated with EPI sequences. Spatial smoothing is performed using a median filter of appropriate window size and then the image is compressed to 8-bits to reduce sensitivity to noise bias. Morphological processing is applied to create and label a binary image. This image will be overlaid on the initial image to mask out both the real and ghost cord. Histogram-based and gray level co-occurrence texture measures will extract relevant information from both cords to remove the ghost artifact. This is achieved using a neuro-adaptive fuzzy logic system.

After ghost removal and spatial smoothing of the image, step 3.c.v details that the coregistration and motion correction of all resultant image volumes using mutual information-based methods and variable degrees of freedom based on diffusion data.

Registration/realignment is a critical step in ensuring that proper voxel to voxel correspondence is achieved for each directional image to provide the most accurate tensor fit. Segmented structural images will be used to align the structural and functional images as well.

After segmented structural images are utilized to align the structural and functional images, step 3.c.vi utilizes an automated quality control check will be performed for rejection of low signal/attenuated slices or artifactually contaminated slices through subject specific, adaptive threshold definition. This will further enhance the accuracy of the tensor fit.

Finally, step 3.c.vii outlines that the tensor estimation is the step that characterizes and quantifies the diffusion information contained within the acquired, and now preprocessed dataset. DTI analysis is the simplest as the model assumes an ideal Gaussian water distribution and each voxel is considered a single compartment. Kurtosis analysis is a refinement in that while it also assumes a single compartment, the underlying displacement distribution is measured in terms of its non-gaussianity. Neurite Orientation Dispersion and Density Imaging (NODDI) is the most sophisticated estimation scheme that is a three-compartment model broken up into CSF, white matter, and gray matter. This more rigorous model enables the quantification of neurite orientation and neurite density within a given voxel. The combination of these analyses forms the multispectral dataset that is utilized to generate the input to the AI module for functional spinal cord characterization, visualization and operative methods for repair to a damaged spinal cord.

However, in order to generate a spatial map and to provide new data that can be analyzed with the AI tools described here, for classification of a novel image as healthy or abnormal, we must collect the unknown MRI data in a consistent manner. Accordingly, in certain applications, Outlier rejection is an iterative weighting approach that seeks to remove datapoints/voxels that will skew results. It is an additional correction scheme embedded in the tensor estimation algorithm to provide another layer of accuracy.

After the preprocessing module is completed, the pattern recognition module is utilized to generate structural data. In Step 3.d, the Quantitative maps generated by the preprocessing module will be then fed into the Pattern Recognition (Texture) Module.

To meet the limitations of the pattern recognition module (3.d), four steps are necessary. Step 3.d.i. confirms that diffusion based quantitative maps, segmented structural images, and defined Regions of Interest (ROI) will be fed into four different texture blocks for image feature extraction. These features will facilitate a more comprehensive characterization of the diffusion and structural data.

These diffusion-based maps are generated via four additional steps:

Step 3.d.i.1: The histogram-based block will investigate the distribution of numerical values of interest, which may include the mean, standard deviation, kurtosis, etc. of the pixel/signal values contained within the ROI.

Step 3.d.i.2: The $2^{nd}$ order texture block will use a predefined window to calculate quantifiable image characteristics using a gray level co-occurrence matrix (GLCM) ranging from 0-135 degrees. These characteristics include homogeneity, correlation, and energy, as examples.

Step 3.d.i.3: The higher order texture block will look at diagonal, horizontal, and vertical wavelet decompositions of the image defined by the ROI. Values such as mean and energy, to name a few, will be determined for each wavelet component.

Finally, step 3.d.i.4: Geometric feature extraction such as edge and corner definition will also be done to collect further information.

After the steps of the diffusion based quantitative maps, statistical testing is performed, according to step 3.d.ii:

Statistical testing will be performed on each of the extracted features calculated from the four texture blocks. Feature vectors will be fed to the statistical module to evaluate their significance. A predefined statistical threshold will be used to select only the features of most importance.

Finally, in step 3.*e*, relevant feature extraction output will proceed to an adaptive CNN based classification system for injury and severity measure. This allows for the creation of a 3-dimensional predictive axonal damage map for quantitative characterization and visualization of the spinal cord for importation in surgical guidance systems in step 3.*f* wherein a compatible neuronavigational system output will be generated that is comprised of a three-dimensional predictive axonal damage map that provides a quantitative characterization and visualization of the spinal cord for surgical guidance and assessment.

Ultimately, the spinal cord level assessments provided by the AI system will be taken and overlaid on a three-dimensional reconstruction of the subject/patient's spinal cord as shown in FIG. 4. Confidence levels as determined by the AI module are represented on a color scale, with the hotter colors indicating a higher injury likelihood. In an alternative to colors, a number scale may point to the generated image, with a scale of 1-10, or 1-100 defining the likelihood of injury. Extension of this concept would allow for the partitioning of specific spinal cord white matter columns so that all white matter quantified at each level could be assigned its own likelihood estimate to provide a comprehensive location and level assessment for the surgeon. This would then allow the surgeon to localize injury and choose candidate sites for stem cell therapies, for example, both prior to and during the surgical procedure.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of generating a quantitative characterization of injury presence and status of spinal cord tissue using an adaptive CNN system for use in diagnostic assessment, surgical planning, and therapeutic strategy comprising:
   preprocessing for artifact correction of diffusion based, spinal cord MRI data;
   training an adaptive CNN system with healthy spinal cord images obtained by imaging a first population of healthy, typically developed spinal cord subjects and abnormal spinal cord images obtained by imaging a second population of subjects and subjects with spinal cord injury;
   evaluating a novel, diffusion-based MRI image for injury biomarkers using the adaptive CNN system;
   generating a three-dimensional predictive axonal damage map for quantitative characterization and visualization of the novel, diffusion-based MRI image; and
   transmitting the healthy spinal cord images and the abnormal spinal cord images back to a central database for continued improvement of the adaptive CNN system training.

2. The method of claim 1 further comprising:
   capturing and storing diffusion-sensitized MRI data, such data including at least one of: Diffusion Tensor Imaging (DTI) data, Diffusion Kurtosis Imaging (DKI) data, Neurite Orientation Dispersion and Density Imaging (NODDI) data, Other higher-order diffusion sampling schema;
   correcting artifacts of the diffusion-based MRI data using a process selected from the group consisting of noise reduction, eddy current correction, segmentation of the spinal cord, ghost artifact removal, coregistration and motion correction, realignment, and automated image quality control;
   estimating and calculating a diffusion tensor, kurtosis tensor, and multi-compartment models using an iteratively-reweighted outlier rejection scheme;
   analyzing a texture to extract relevant $1^{st}$ order, $2^{nd}$ order, higher order, as well as geometric image features for texture training of the adaptive CNN system; and
   using processed healthy volunteer and injured spinal cord datasets for continued diagnostic training of the adaptive CNN system.

3. The method of claim 1, wherein the pre-processing comprises a step selected from the group consisting of: noise reduction based on a principal component analysis (PCA) method for signal decomposition and elimination of noise, eddy current correction based on estimation of the eddy current (EC) distortion field, segmentation of the cord using histogram thresholding for tissue classification, morphological processing, and region growing techniques, ghost artifact removal based on texture analysis and automated classification using neuro-adaptive fuzzy logic, co-registration and realignment based on maximized mutual information and a variable degree of freedom transformation and combinations thereof.

4. The method of claim 1, wherein the pre-processing module comprises an automated image quality control step based on local SNR characteristics, Euclidean metrics, and tissue contrast.

5. The method of claim 1, wherein the pre-processing module comprises a tensor estimation step unique to the sampling scheme used.

6. The method of claim 1, wherein the pre-processing module comprises an outlier rejection step based on iteratively reweighting individual diffusion sensitized images based on residuals during the tensor estimation process.

7. The method of claim 1, wherein after completion of a pre-processing module, a pattern recognition module is performed.

8. The method of claim 1, wherein a pattern recognition module comprises histogram textures selected from the group consisting of image intensity, variance, entropy, skewness, and kurtosis.

9. The method of claim 1, wherein a pattern recognition module comprises $2^{nd}$ order textures selected from the group consisting of co-occurrence matrix contrast, homogeneity, correlation, and energy at 45° intervals.

10. The method of claim 1, wherein a pattern recognition module comprises higher order textures selected from the group consisting of mean, variance, entropy, and energy of vertical, horizontal, and diagonal wavelet components.

11. The method of claim 1, wherein a pattern recognition module comprises geometric textures selected from the group consisting of edge, corner, roundness, elasticity, and solidness.

12. The method of claim 1, wherein a pattern recognition module comprises histogram textures, $2^{nd}$ order textures, higher order textures, and geometric textures, and statistical testing of the same to determine feature relevance for the adaptive CNN system.

13. The method of claim 1, where training an adaptive CNN system using the captured and processed diffusion sensitized MRI data for normal and abnormal subjects.

14. The method of claim 1, wherein the trained adaptive CNN system classifies imaged tissue from patients as likely to be injured or not likely to be injured based on the aforementioned training using normative diffusion sensitized MRI data.

15. The method of claim 1, further comprising generating a quantitative, three-dimensional predictive axonal damage map for the spinal cord, wherein the trained, adaptive CNN system provides quantitative information needed to characterize a presence, location, and extent of spinal cord injury on a per subject basis.

16. The method of claim 1, further comprising identifying injury to a spinal cord, wherein the predictive axonal damage map is usable by clinicians, surgeons, physical therapist, PM&R staff for reporting, surgical planning, and therapeutic strategy.

17. The method of claim 1, wherein the predictive axonal damage map is imported to a neuronavigational system;
   wherein the predictive axonal damage map is imported as a 3-D image to the neuronavigational system; and
   wherein the predictive axonal damage map is overlaid onto conventional, structural MRI imaging to provide a clinician with a real time view, location, and extent of tissue damage during surgical procedures.

18. The method of claim 1, wherein diffusion sensitized image features are transmitted and stored on a centralized database for continued improvement of the adaptive CNN system training.

19. A method of treating a patient exhibiting spinal cord damage comprising: use of the method of claim 18 to generate a predictive axonal damage map, wherein said predictive axonal damage map is imported into a neuronavigational system for performing a surgical procedure.

* * * * *